United States Patent [19]

Tomioka et al.

[11] 4,273,902

[45] Jun. 16, 1981

[54] DENTAL SILICONE COMPOSITIONS AND THE METHOD OF USING THE SAME

[75] Inventors: Kentaro Tomioka, Chofu; Kazuhiro Watanabe, Kamifukuoka; Eiji Iwata, Tokyo, all of Japan

[73] Assignee: G-C Dental Industrial Corp., Tokyo, Japan

[21] Appl. No.: 48,979

[22] Filed: Jun. 15, 1979

[30] Foreign Application Priority Data

Jun. 30, 1978 [JP] Japan .................................. 53-78745

[51] Int. Cl.$^3$ ............................................. C08L 83/06
[52] U.S. Cl. ...................................... 525/478; 106/35; 525/475; 525/479; 528/15; 528/31
[58] Field of Search ...................... 525/475, 478, 479; 528/31, 15; 106/35

[56] References Cited

U.S. PATENT DOCUMENTS

| | | | |
|---|---|---|---|
| 2,632,013 | 3/1953 | Wagner et al. | 260/448.2 H |
| 4,035,453 | 7/1977 | Hittmair et al. | 525/478 |

*Primary Examiner*—Wilbert J. Briggs, Sr.
*Attorney, Agent, or Firm*—Oblon, Fisher, Spivak, McClelland & Maier

[57] ABSTRACT

Disclosed is a room-temperature setting dental silicone composition comprising an organovinylpolysiloxane, an organohydrogen polysiloxane, a catalyst for promoting the addition reaction therebetween, hydrophobic fillers and finely divided palladium and/or an alloy thereof. The palladium and/or palladium alloy should be used in amounts of 0.5 ppm or more relative to the total silicone polymer components. The organohydrogen polysiloxane and catalyst are separately stored. In use, the remaining components are mixed with said two components in any order.

2 Claims, No Drawings

DENTAL SILICONE COMPOSITIONS AND THE METHOD OF USING THE SAME

BACKGROUND OF THE INVENTION

The present invention relates to room-temperature setting silicone composition for taking dental models (silicone impression material) including as fundamental components (a) an organopolysiloxane having in its molecule at least two vinyl groups and (b) an organohydrogen polysiloxane having in its molecule hydrogen atoms bonded to at least two silicone atoms, and further including (c) a known platinum-based catalyst, (d) hydrophobic fillers, and (e) finely divided palladium and/or a finely divided palladium alloy containing more than 10% by weight of palladium, and a method of using the same.

Heretofore, the organopolysiloxane-based material for taking dental impressions has widely been used as a silicone impression material. More particularly, such a material employs a dihydroxy polyorganosiloxane as a base, an alkyl silicate or polyalkyl silicate as a cross-linking agent and an organic tin compound as a condensation catalyst, which are mixed or kneaded together to effect a condensation reaction therebetween, thus forming an elastomer. However, such a system is disadvantageous in that the elastomer evolves volatile components such as alcohols produced in the condensation reaction and unreacted alkyl silicate to undergo a gradually increasing change in dimensions upon setting, and still gives out an offensive odor peculiar to the liquid catalyst.

Currently, a system for producing elastomers from organopolysiloxanes each having in its molecule vinyl groups and organohydrogen polysiloxanes each having in its molecule hydrogen atoms bonded to silicone atoms by setting them by an addition reaction with the aid of a catalyst at room temperature has been developed and found to have marked advantages over the prior art silicone impression materials. That is to say, this silicone impression material undergoes a linear shrinkage in the order of only about 0.1%, i.e., about one-fourth to one-tenth or less of that of the conventional silicone impression materials 24 hours after an impression has been taken. Accordingly, it is possible to prepare a model having a high dimensional accuracy. In addition to their tasteless and odorless, the organopolysiloxanes having in their molecues vinyl groups and the organohydrogen polysiloxanes having in their molecules hydrogen atoms bonded to silicone atoms can be mixed and kneaded in equal amounts as their silicone polymer paste products have the same viscosity. From this fact, they are found to excel in dental performance and workability.

In the reaction process during which the organopolysiloxanes having vinyl groups and the hydrogen atoms of the organohydrogen polysiloxanes are subjected to an addition reaction to form elastomers, however, hydrogen gas is partially evolved. When a gypsum slurry is poured into an impression just after the impression has been taken, a number of pores are formed on the set gypsum model due to the hydrogen gas, thus producing a spongy surface thereon. In most cases, such a model was not substantially available to practical dentistry. In order to prevent such a spongy surface from being formed on the gypsum model by the hydrogen gas, it was required to pour a gypsum slurry into a silicone impression taken after the impression has been allowed to stand for more than 2 hours, has been degassed by heating, or has been treated under reduced pressure for more than 5 minutes. This operation was troublesome in making the model, and wasted much time. Furthermore, this operation did not only require a special device, but resulted in a fear that the dimensional accuracy of the model is made worse.

SUMMARY OF THE INVENTION

As a consequence of comprehensive investigation made with a view to preventing generation of hydrogen gas, it has been found that the presence of fine powder which is mainly based on metallic palladium in the composition causes excess hydrogen gas which does not take part in any reaction to be completely absorbed therein in a very short time interval without inhibiting the addition reaction and adversely affecting the shelf-life of the composition.

An advantage of the silicone composition for taking dental impressions according to the present invention is that a very smooth surface can be produced on a gypsum model which is poured and set on the surface of the silicone material for taking a dental impressions which have been inserted in the oral cavity and set therein.

DETAILED DESCRIPTION OF THE INVENTION

The fundamental components according to the present invention comprise:

(a) an organopolysiloxane having in its molecule at least two vinyl groups, (b) an organohydrogen polysiloxane having in its molecule hydrogen atoms directly bonded to at least two silocone atoms, (c) a catalyst for accelerating the addition of the hydrogen atoms bonded to the silicone atoms with the vinyl groups (for example, platinum-based catalysts), (d) hydrophobic fillers and, if necessary, known additives, and (e) finely divided palladium powder having an action on the absorption of nascent hydrogen at room temperature.

So long as the components a, b, c, d and e are separated into two parts, one comprising b and the other c, the respective components a, d and e may be incorporated into either or both of the components b and c. Alternatively, the components a, d and e may be mixed together as a third component. It should be noted that, if the impression composition is capable of being cured by mixing the two components b and c therewith, then all available mixing methods are used for this purpose.

The metal powder used as component e is finaly divided palladium and/or palladium alloy having a particle size of less than 0.5 mm. This powder should preferably be powdered as minutely as possible, and is more preferably ground to a powder having a particle size of less than 10 microns. For better results, the surface area of the metal is maximized by pulverizing it on a carrier composed of a suitable active material.

Of the composition according to the present invention, the organopolysiloxane having vinyl groups which serves as a component may be a known organopolysiloxane having in its molecule at least two vinyl groups such as that having vinyl terminated triorganosiloxyl groups or having structure such as terminal groups closed by hydroxyl groups and a skeleton comprising a $(CH_3)(CH_2{=}CH)SiO$ unit and a $R_2SiO$ unit (wherein R denotes a monovalent saturated hydrocarbon radical such as methyl, ethyl, butyl and phenyl radicals).

The organohydrodiene polysiloxane serving as component b may be that having in its molecule hydrogen atoms bonded to at least two silicone atoms. This compound is known and includes siloxane copolymers having different polymerization degrees and their both terminals closed by trialkylsilyl or dialkylhydrogensilyl radicals.

Component c may be hydrogen chloro platinic acid, or an alcohol or aldehyde compound thereof, or a complex thereof with various olefines which are known as the catalysts for the setting reaction of components a and b, and is normally added to the elastomer compoistion in a range of 0.5 to 500 ppm calculated as platinum. In addition, use may be made of rodium compounds as well as cobalt carbonyl and manganese carbonyl as the catalysts for accelerating the addition reaction.

Component d includes conventional fillers such as finely divided quartz, diatomaceous earth, calcium carbonate, gypsum, aluminium silicate, titanium oxide, zinc oxide and zirconium silicate.

While the combination of the aforesaid four components is well known in the art, the present invention is characterized in that the dental impression material having excellent properties can be provided by using palladium based fine powder as a fifth component together with the aforesaid four components. The fine powder of palladium and/or palladium alloys used here preferably has a particle size of less than 0.5 mm. Better results are obtained if the powder has a particle size of less than 10 microns.

As metals capable of absorbing hydrogen other than palladium, mentioned are platinum, rhodium, rubidium, iridium, molybdenum, aluminium, copper, silver, iron, nickel, cobalt, zirconium, titanium, tantalum, vanadium, niobium and rare earth metals. While these metals are separately used in the form of fine powder to decrease pores formed on the surface of the gypsum model by hydrogen gas generated from the impression material, it is difficult to eliminate the pores in a short time interval even by using said metals in considerable amounts. Thus, these metals are inferior to palladium. However, since the use of these powdery metals capable of absorbing hydrogen together with the palladium powder results in an increase in the effect of the latter, one or more of these metals may be used with a view to decreasing the amount of palladium.

As the palladium alloys, use may be made of alloys containing at least 10% of palladium, but preference is given to palladium alloys containing one or more of the aforesaid metals capable of absorbing hydrogen. In particular, the palladium alloys containing one or more of silver, copper, nickel and cobalt which can form a complete solid solution with palladium have a favorable effect.

Thus, the gist of the present invention is to provide an elastomer forming a dental impression material effective in taking models by subjecting to reaction and setting two siloxane components, an organopolysiloxane having in its molecule vinyl groups and an organohydrogen polysiloxane having in its molecule hydrogen atoms bonded to silicone atoms, at room temperature in the presence of a catalyst, at least one of said components being previously incorporated with palladium and/or a palladium alloy in the form of fine powder so as to absorb hydrogen gas produced in the reaction.

The present invention will now be described in detail with reference to possible examples in which all the parts are given by weight.

EXAMPLE 1

Component (i) was prepared by mixing together 500 parts of dimethyl polysiloxane having a viscosity of 120 poises at 25° C. and a terminal vinyldimethylsiloxy group, 150 parts of finely divided quartz, 50 parts of calcium carbonate, 0.1 parts of a platinum/siloxane complex and 1 part of palladium powder having an average particle size of 0.1 mm.

Next, as component (ii) was prepared hydrogenmethyl polysiloxane having a viscosity of 30 poises. A mixture obtained by mixing 7 parts of component (i) with 1 part of component (ii) on a mixing plate was inserted under suitable pressure in the mouth. The mixture was then set in five minutes to form an elastomer. Immediately after this impression was washed with water, a slurry obtained by mixing 100 g of a dental stone available under the trade name "PLASTONE" with 30 ml of water was poured into the impression. After 30 minutes, a model was removed from the impression.

EXAMPLE 2

Using a kneader, component (i) was prepared by mixing together 500 parts of hydroxyl-terminated vinylmethyl polysiloxane having a viscosity of 250 poises at 25° C., 150 parts of finely divided quartz, 50 parts of zirconium silicate, 0.05 parts of hydrogen chloroplatinicacid, 0.001 parts of palladium powder having an average particle size of 7 microns and 3 parts of nickel powder having an average partice size of 6 microns. Next, component (ii) was prepared by mixing together 300 parts of hydroxyl-terminated vinylmethyl polysiloxane having a viscosity of 250 poises, 200 parts of hydrogenmethyl polysiloxane having a viscosity of 320 poises and 150 parts of finely divided quartz by means of a kneader.

A mixture of the equal weights of components (i) and (ii) obtained on a mixing plate was inserted under suitable pressure in the mouth. The mixture was then set in three minutes to form a complete elastomer. Just after this impression was washed with water, a slurry obtained by mixing 100 g of a high strength dental stone available under the trade name "SURSTONE" with 24 ml of water was poured into the impression. After the lapse of 30 minutes, a model was removed from the impression.

EXAMPLE 3

Using a kneader, component (i) was prepared by mixing together 300 parts of vinyldimethylsiloxy-terminated vinylmethyl polysiloxane having a viscosity of 350 poises at 25° C., 600 parts of finely divided quartz, 50 parts of calcium carbonate, 0.07 parts of a platinum/alcohol complex and 0.1 parts of alumina powder having an average particle size of 2 microns onto which 7% by weight of palladium (based on alumina) was supported. Next, component (ii) was prepared by mixing together 200 parts of vinylmethylsiloxy-terminated vinylmethyl polysiloxane having a viscosity of 350 poises, 100 parts of hydrogenmethy polysiloxane having a viscosity of 300 poises, 600 parts of finely divided quartz and 70 parts of calcium carbonate by means of a kneader.

A mixture of the equal weights of components (i) and (ii) kneaded and mixed on the palm of a hand was inserted under pressure in the mouth. The mixture was then set in three minutes to form a hard elastomer having a Shore hardness of 75. Immediately upon washing with water, this impression was poured with a slurry obtained by mixing 100 g of a dental stone available under the trade name "NEW PLASTONE" with 25 ml of water. After the lapse of 30 minutes, a model was removed from the impression.

EXAMPLE 4

Example 2 was repeated, but in place of 0.1 parts of the palladium powder having an average particle size of 7 microns and 3 parts of the nickel powder having an average particle size of 6 microns, use was made of 0.02 parts of fine powder having an average particle size of 10 microns, said fine powder being prepared by subjecting a palladium alloy consisting of 30% of palladium, 60% of silver and 10% of copper to a melting-spray method in a nitrogen current. In the same manner as in Example 2, a model was prepared from a mixture of the equal weights of components (i) and (ii).

EXAMPLE 5

A model was prepared according to Example 3, but the alumina powder having an average particle size of 7 microns onto which 7% by weight of the metallic palladium was supported was used in an amount of 0.01 parts in place of 0.1 parts.

COMPARATIVE EXAMPLE 1

A model was prepared according to Example 3, but the alumina powder having an average particle size of 2 microns onto which 7% by weight of the metallic palladium was supported was removed from component (i).

In the foregoing Examples and Comparative Example, the same mouth was employed. Each model thus obtained was observed under a stereoscopic microscope to count the number of pores formed on the surface thereof. In most cases, the pores had a diameter of about 0.2 mm. The surface of the gypsum model was separated into three limited portions, i.e., the gum, tooth and palate portions. Each portion was observed at three points to determine the number of pores per cm$^2$. The number of pores thus determined was averaged for estimation.

| Number of Pores | |
|---|---|
| 0 to 2 | more effective |
| 3 to 20 | effective |
| 30 or more | noneffective |

The reason why the number of pores of 0 to 2 is estimated to be more effective resides in the fact that, due to the strong water repellency of the surface of the silicone impression material, the formation of pores cannot be avoided under the condition for pouring the gypsum slurry. Thus, when the number of pores is 2 or less, the pores are regarded as being completely eliminated from the standpoint of evaluation. The number of pores of 3 to 20 is also estimated to be effective since the then model can practically be used. On the other hand, 50 to 150 pores per unit surface area are formed on the surface of a model outside the scope of the present invention. Such a model is not put to practical use and hence, the number of pores of 30 or more is estimated to be noneffective.

TABLE 1

| | Gum portion | Tooth portion | Balate portion | Average | Estimation |
|---|---|---|---|---|---|
| Ex. 1 | 0 | 0 | 0 | 0 | More Effective |
| 2 | 1 | 0 | 1 | 1 | More Effective |
| 3 | 0 | 0 | 1 | 0 | More Effective |
| 4 | 3 | 0 | 2 | 2 | More Effective |
| 5 | 7 | 3 | 6 | 5 | Effective |
| Comparative Ex. 1 | 156 | 56 | 97 | 103 | Noneffective |

The figures in the table denote the number of pores per cm$^2$ of the dental stone surface when the dental stone is poured into the surface of the silicone impression material.

The composition obtained in Example 5 contains 1.2 ppm of palladium relative to the total silicone polymer components. The obtained gypsum model has been found to have few pores at the tooth germ and palate portions. As shown in Example 2, however, it has been found that the addition of 0.9 ppm of palladium and 0.3% of nickel powder renders possible completely elimination of pores. Hence, according to the present invention, the minimum concentration of the palladium-based powder relative to the total silicone polymer components is limited to 0.5 ppm.

In the gypsum model obtained according to Example 4 using an alloy containing 30% by weight of palladium, a considerable number of pores have been found to be removed. However, since the action of the alloy drops steeply with a decrease in the palladium content, the minimum concentration of palladium in the alloy is restricted to 10%.

As will be apparent from the above-mentioned results, the present invention makes it possible to prepare an uniform and smooth surface on a gypsum model which is free from any pores and heance, is of practical value by the conventional method of fabricating models available to dentistry. This model is also free from the disadvantage of the prior art addition type silicone impression material, and excels in dimentional stability and workability. Thus, the present invention has succeeded in the provision of a novel addition type silicone impression material which is by far superior in many properties to the known dental impression material.

While the invention has been described with reference to specific examples thereof, it is apparent to one skilled in the art various modifications and changes can be made therein without departing from the spirit and scope of the present invention.

What is claimed is:

1. A room temperature setting dental silicone composition comprising (a) an organopolysiloxane having in its molecule at least two vinyl groups, (b) an organohydrogen polysiloxane having in its molecule hydrogen atoms bonded to at least two silicone atoms, (c) a catalyst for accelerating the addition of the hydrogen atoms bonded to the silicone atoms with respect to the vinyl groups, and (d) hydrophobic fillers and characterized in that it further includes 0.5 ppm or more of finely divided palladium and/or a finely divided palladium alloy containing 10% by weight or more of palladium relative to the total silicone polymer components, which absorbs hydrogen gas generated in the reaction of the polysiloxane having vinyl groups with the polysiloxane having Si-H bonds, without inhibiting the addition reaction.

2. In a method of using dental silicone composition comprising (a) an organopolysiloxane having in its molecule at least two vinyl groups, (b) an organohydrogen polysiloxane having in its molecule hydrogen atoms bonded to at least two silicone atoms, (c) a catalyst for accelerating the addition of the hydrogen atoms bonded to the silicone atoms with respect to the vinyl groups, (d) hydrophobic fillers and (e) 0.05 ppm or more of finely divided palladium and/or a finely divided palladium alloy containing 10% by weight or more of palladium relative to the total amount of said four components (a) through (d), said method being characterized in that components (b) and (c) of said five components are separately stored, and the remaining component (a), (d) and (e) are mixed with the former components in any order before or during use said palladium or palladium alloy having the property of absorbing hydrogen gas generated in the reaction of the polysiloxane having vinyl groups with the polysiloxane having Si-H bonds, without inhibiting the addition reaction.

* * * * *